(12) United States Patent
Cardinale et al.

(10) Patent No.: US 6,644,098 B2
(45) Date of Patent: Nov. 11, 2003

(54) HEATED ELECTRODE REFRIGERANT DETECTOR UTILIZING ONE OR MORE CONTROL LOOP

(75) Inventors: Dennis Cardinale, Plantation, FL (US); Robert Zubik, Miami, FL (US)

(73) Assignee: Advanced Test Products, Inc., Miramar, FL (US)

( * ) Notice: Subject to any disclaimer, the term of this patent is extended or adjusted under 35 U.S.C. 154(b) by 159 days.

(21) Appl. No.: 09/838,169

(22) Filed: Apr. 19, 2001

(65) Prior Publication Data

US 2002/0092341 A1 Jul. 18, 2002

Related U.S. Application Data

(60) Provisional application No. 60/262,525, filed on Jan. 18, 2001.

(51) Int. Cl.[7] .................. H05B 39/04; G01N 27/04; G01N 27/407; G01N 27/46; G01N 33/22

(52) U.S. Cl. .................. 73/25.01; 73/25.05; 73/31.05; 422/90; 422/98; 422/109; 324/443

(58) Field of Search .................. 73/25.01, 25.05, 73/23.2, 31.05; 422/98, 90, 109; 324/98, 109, 610, 464, 443–444

(56) References Cited

U.S. PATENT DOCUMENTS

| | | | | |
|---|---|---|---|---|
| 2,404,474 A | * | 7/1946 | Collins | 73/25.01 |
| 3,347,635 A | * | 10/1967 | McKee | 23/232 E |
| 3,449,939 A | * | 6/1969 | Monomakhoff | 73/25.01 |
| 3,607,084 A | * | 9/1971 | Mackey et al. | 23/232 E |
| 3,616,678 A | * | 11/1971 | Batzies | 73/25.01 |
| 3,739,260 A | | 6/1973 | Schadler | 324/33 |
| 3,912,967 A | | 10/1975 | Longenecker | 315/107 |
| 3,991,360 A | | 11/1976 | Orth et al. | 324/33 |
| 4,151,641 A | | 5/1979 | Mitoff | 29/611 |
| 4,157,311 A | | 6/1979 | Orth et al. | 252/408 |
| 4,171,341 A | | 10/1979 | Morgan | 422/98 |
| 4,203,199 A | | 5/1980 | Morgan | 29/612 |
| 4,237,721 A | * | 12/1980 | Dolan | 73/23.2 |
| 4,244,918 A | * | 1/1981 | Yasuda et al. | 422/95 |
| 4,298,573 A | * | 11/1981 | Fujishiro | 422/94 |
| 4,305,724 A | | 12/1981 | Micko | 23/232 |
| 4,327,054 A | * | 4/1982 | Yasuda et al. | 422/95 |
| 4,520,653 A | * | 6/1985 | Kaiser | 73/23.2 |
| 4,609,875 A | | 9/1986 | Jeffers | 324/455 |
| 4,879,546 A | | 11/1989 | Dunham et al. | 340/632 |
| 4,910,463 A | | 3/1990 | Williams, II et al. | 324/468 |
| 5,104,513 A | | 4/1992 | Lee et al. | 204/425 |
| 5,198,774 A | | 3/1993 | Williams, II et al. | 324/468 |
| 5,226,309 A | | 7/1993 | Stetter et al. | 73/31.06 |
| 5,284,569 A | | 2/1994 | Lee et al. | 204/425 |
| 5,297,419 A | * | 3/1994 | Richardson | 73/25.03 |
| 5,351,037 A | | 9/1994 | Martell et al. | 340/632 |

(List continued on next page.)

OTHER PUBLICATIONS

Yokogawa Corporation of America—Operation Manual for Top Gun, Model No. H10Xpro "Refrigerant Leak Detector", (8 pages).

Leybold Inficon Inc.—User's Manual for D–TEK Refrigerant Leak Detector, (10 pages).

Primary Examiner—Helen Kwok
Assistant Examiner—David J. Wiggins
(74) Attorney, Agent, or Firm—Baker & Hostetler LLP

(57) ABSTRACT

A gas detector for sensing the presence of at least one predetermined gas is operative in conjunction with a electrical power source and includes a detection circuit, a temperature controller, and a electrical current controller, wherein the detection circuit includes a sensing device having first and second electrodes, the first electrode being connected to the power source for heating the first electrode, the temperature controller is operatively connectable to the detection circuit for maintaining a temperature of the first electrode at a predetermined magnitude, and the current controller is operatively connectable to the detection circuit for maintaining a current in the second electrode at a predetermined magnitude.

20 Claims, 3 Drawing Sheets

U.S. PATENT DOCUMENTS

| | | | |
|---|---|---|---|
| 5,400,015 A | 3/1995 | Liebermann | 340/632 |
| 5,444,435 A | 8/1995 | Williams, II et al. | 340/632 |
| 5,448,905 A | 9/1995 | Stetter et al. | 73/31.05 |
| 5,490,413 A | 2/1996 | Atkinson | 73/40 |
| 5,608,384 A | 3/1997 | Tikijian | 340/632 |
| 5,841,021 A | 11/1998 | De Castro et al. | 73/23.2 |
| 5,858,739 A * | 1/1999 | Williams | 436/151 |
| 5,897,836 A * | 4/1999 | Martell et al. | 422/90 |
| 5,932,176 A | 8/1999 | Yannopoulos et al. | 422/98 |
| 5,969,231 A * | 10/1999 | Qu et al. | 73/31.05 |
| 6,085,576 A | 7/2000 | Sunshine et al. | 73/29.01 |
| 6,289,719 B1 * | 9/2001 | Bloemer et al. | 73/23.21 |
| 6,336,354 B1 * | 1/2002 | Suzuki et al. | 73/31.05 |

* cited by examiner

HEATED ELECTRODE REFRIGERANT DETECTOR UTILIZING ONE OR MORE CONTROL LOOP

CROSS-REFERENCE TO RELATED APPLICATION

This application is entitled to the benefit of, and claims priority to, U.S. patent application Ser. No. 60/262,525, filed Jan. 18, 2001 and entitled "HEATED ELECTRODE REFRIGERANT DETECTOR UTILIZING ONE OR MORE CONTROL LOOP."

BACKGROUND OF THE PRESENT INVENTION

1. Field of the Present Invention

The present invention relates generally to the field of gas sensors, and, in particular, to the art of detecting halogenated refrigerants by applying control theory to an improved "heated electrode" technology to control the operation of the detector using an advanced sensing device and one or more control loops.

2. Background Art

Gas detectors for sensing the presence of halogenated gases and other gases are well known. FIG. 1 shows prior art gas detector type suitable for this purpose, commonly referred to as a "heated electrode" sensor. This sensor utilizes a cathode wire and an anode wire made of platinum, palladium or an alloy thereof. Typically, the cathode is repeatedly coated with a ceramic material such as a mixture of an alkali metal silicate and oxides of aluminum or silicon, with a drying period between each coat, and then inserted into an anode coil formed by several turns of the anode wire. The anode/cathode assembly is then coated further with the same mixture, except for the ends of the anode and the exposed end of the cathode, and dried. After the final drying, the anode/cathode assembly is fired in a kiln and then installed in a housing, with the exposed ends of the anode and cathode connected to anode contacts and a cathode contact, respectively. The final assembly is then energized and biased over many hours by applying a electrical current through the anode coil and a voltage across the anode coil to the cathode wire.

The ceramic forms an electrically resistive layer between the electrodes. When heated by an electrical current passing through a first of the electrodes, an outer layer depleted of ions develops along the electrodes. When this layer is exposed to reactive gases like halogen, ions flow across the depletion zone and the conductivity of the device is increased. Thus, the presence of halogenated gases may be determined by monitoring the current generated through the second electrode, referred to as the bias current, for a sudden increase in magnitude created by introducing the device to such gases. These sensors are commonly utilized by technicians to determine whether a refrigerant leak exists and to pinpoint its source.

Advantageously, heated electrode sensors have low electrical power requirements and good sensitivity, and such sensors exhibit excellent selectivity in that they tend to ignore most chemical vapors which may be present in a typical test environment, as well as water vapor. Unfortunately, prior art heated electrode sensors also suffer a number of drawbacks. First, and most significantly, the bias current is dependent not only upon the presence or absence of halogenated molecules at the electrodes, but by the temperature of the device as well. Thus, sudden changes in temperature are frequently misinterpreted as an indication of the presence of halogenated molecules because their respective effects are the same: each causes an increase in the bias current of the sensor.

U.S. Pat. No. 4,305,724 to Micko (the "'724 patent") discloses a combustible gas detection system including a sensor temperature control system. The detection system includes a sensor element having active and reference sensors for detecting combustible gases, a controlled current source for providing electrical power to the sensor element, a voltage-to-duty cycle converter for providing a square wave control signal of variable duty cycle and a bypass switch for bypassing the active sensor element in response to the control signal. By increasing or decreasing the duty cycle, the amount of electrical energy flowing to the active element is likewise affected and the temperature of the active sensor may correspondingly be either upwardly or downwardly biased. When the presence of combustible gas begins to cause the temperature of the active sensor to increase, the increase is detected by the temperature control system and the duty cycle is adjusted to counteract the increase and maintain the temperature constant.

Unfortunately, the detection system of the '724 patent suffers from some drawbacks. First, the detection system of the '724 patent requires the use of a reference sensor. Perhaps more importantly, the temperature control system is used only to equalize the temperature of one sensor with respect to the other sensor. In particular, it includes no means for measuring the absolute temperature of either sensor, or for independently setting the absolute temperature of either sensor to a particular chosen value. This is sufficient in the active sensor type of the '724 patent because the presence of the gas sought may generally be indicated merely by the heat given off by the oxidation process, as indicated by the temperature of the active sensor compared to that of the reference sensor. This characteristic makes the active sensor of the '724 patent impervious to fluctuations in absolute temperature due to ambient conditions. However, in heated electrode refrigerant detector systems, the presence of the gas sought is indicated generally by an increase in bias current, which is also affected by the ambient temperature of the sensor. As a result, a heated electrode refrigerant sensor using the temperature control system of the '724 patent would still be affected by ambient conditions because it is incapable of controlling the absolute temperature of the sensor. In addition, the absolute temperature of the sensor cannot be controlled to prevent damage during warm-up of the system and the like. Thus, a need exists for a temperature control system suitable for use with a heated electrode refrigerant detection system which does not make use of a reference sensor and which may be utilized to control the absolute temperature of the heated electrode.

U.S. Pat. No. 3,912,967 to Longenecker (the "'967 patent") discloses a circuit for providing regulation of the absolute temperature of a heater-anode of a refrigerant gas sensor. A power supply outputs two different DC voltage levels, one of which is connected through a transistor switch to the heater-anode coil of a heated electrode gas sensing element. The circuit monitors the approximate absolute temperature of the heater-anode based on its effective resistance. When the absolute temperature of the heater-anode drops enough below a desired value, a temperature regulation circuit closes the switch, and a greater amount of current is supplied to the heater-anode. When the temperature of the heater-anode reaches the desired value again, the temperature regulation circuit opens the switch and a lesser amount of current is supplied to the heater anode. Thus, as the temperature of the sensing element fluctuates, greater or lesser heating may be applied to the heater-anode by the temperature regulation circuit. Unfortunately, although this circuit provides some control over the absolute temperature of a heated electrode refrigerant sensor, the regulation is relatively crude, effectively permitting control only by turning an auxiliary heat source on and off. At best, the temperature of the sensor is thus roughly held in a general range, with the upper approximate limit being the desired temperature and the lower approximate limit being the temperature at which the transistor of the switch is cool enough to allow the auxiliary power supply to be coupled in. At worst, however, such a crude controller may allow the temperature of the sensor to oscillate wildly and even dangerously under certain conditions. Further, the circuit allows no adjustment to be made to the triggering temperatures at which the auxiliary source is turned on or off. Thus, a need exists for a more sophisticated temperature control system suitable for use with a heated electrode refrigerant detection system which allows the temperature of the sensor to be rigidly maintained at a particular absolute value, rather than within a wide range of temperatures, and wherein that value is adjustable.

Another disadvantage of prior art heated electrode sensors is that their lifespans are frequently limited much more than is necessary. It is well known that the operation and lifespan of heated electrode sensors are limited by the number of alkali ions in the sensor. It has been found that the bias current and the rate of depletion of ions are directly related to each other. Thus, as the sensor is used, the ions are depleted, and when no ions are left at all, the sensor is "dead." Unfortunately, the sensitivity of the sensor is directly related to the bias current, and so the greater the sensitivity of the sensor, the more quickly the sensor is used up. Prior art heated electrode sensors fail to take these characteristics into account and are thus used up more quickly than is necessary. In addition, the exposure of prior art sensors to high concentrations of refrigerant, even for a relatively short period of time, causes a correspondingly high bias current which results in an immediate reduction in sensor sensitivity and a considerable shortening of the sensor's lifespan. This effect is known in the industry as "poisoning" the sensor, and no good solution to the problem has yet to be proposed. Finally, despite their limited lifespan, prior art refrigerant detectors provide no means of monitoring or checking the sensor to determine its remaining life.

Some solutions to these problems have been proposed. For example, the H10Xpro Refrigerant Leak Detector, available from the Yokogawa Corporation of America of Newnan, Ga., is a refrigerant leak sensor of the heated electrode type. Like other sensors of this type, the Yokogawa sensor becomes less sensitive over time. The Yokogawa sensor allows users to increase the sensitivity of the sensor by increasing the heat which is applied to the electrode. Because the magnitude of the bias current is dependent not only on the voltage potential between the anode and cathode and the amount of refrigerant present, but is also dependent upon the temperature of the electrode, and because the sensitivity of the sensor is related to the magnitude of the bias current, the sensitivity of the sensor may be improved by raising the temperature of the electrode during operation of the sensor. Yokogawa allows this to be done by manually turning a screw a small amount, presumably to adjust the operating voltage of the electrode. Further, there is a great danger that the user may forget to return the sensor temperature to the manufacturer's setting when he replaces a depleted sensor with a new one, therefore operating the new sensor at a highly elevated temperature and seriously reducing the life of the new sensor. An improved sensor which continually and automatically adjusts the operation of the electrode to provide sufficient sensitivity over an extended lifetime of the sensor is needed.

U.S. Pat. No. 3,739,260 to Schadler (the "'260 patent") discloses a method of operating a halogen detector of the heated electrode type. A current supply unit supplies current through a current setting means to the electrode to heat the anode, thus creating a fundamental ion current flow between the anode and the cathode. The presence of halogenous gas at the electrode causes an increase in the ion current which is amplified and its magnitude indicated by an indicator and/or an alarm. In addition, another amplifier is connected in a feedback loop between the output of the electrode and the current setting means. When the magnitude of the ion current varies by a predetermined amount, the variable gain amplifier supplies a signal to the current setting means to adjust the heating supply current to the anode in a direction to counteract the variation. Unfortunately, the detector of the '260 patent suffers from some serious drawbacks.

First, because at power-on there is typically a leakage current which flows through the electrode, the feedback loop will operate to adjust the supply current to maintain the ion current at the level of that leakage current. It has been discovered that the leakage current is due to the absorption of moisture while the detector is not in use, and is generally many times larger than the bias current required for normal operation. Therefore, the "variable gain amplifier" described may never provide enough gain at power-on to raise the temperature of the sensor to its desired operating point.

Significant limitations are also placed on the performance of the detector of the '260 patent by the means by which a refrigerant is detected. More particularly, not only is the ion current being controlled by the feedback loop, but it is also the process variable which is monitored for a condition indicating the presence of halogen molecules. Unfortunately, such an approach mandates the use of inherent high-pass filtering artifacts that reduce a signal level change into a time-varying peak which lasts only a certain period of time, even though refrigerant may still be present at the sensor. Further, the detector of the '260 patent is designed to compensate only for relatively slow fluctuations of the ion current and no adjustment is made by the feedback loop for spikes in the magnitude of the ion current which disappear before the end of the period of the gain amplifier is reached. The single process variable approach thus permits short term, high-magnitude fluctuations in the ion current which significantly shorten the lifespan of the sensor. Thus, a more sensitive and longerlasting heated electrode leak detector is needed which uses a control loop and a plurality of process variables to more reliably detect the presence of a refrigerant.

Finally, another drawback of prior art sensing devices is the length of time required to assemble and "burn in" a anode/cathode assembly. Existing methods require both the anode and the cathode to be coated with the ceramic material before assembly and then further coated thereafter and require considerable periods of time for drying between the various coatings. Further, prior art methods require an assembled anode/cathode assembly to first be fired in order to sinter the ceramic material before biasing and the assembly to create a depletion region. A need exists for a manufacturing method which may be completed in a much shorter period of time than is possible using known methods.

SUMMARY OF THE INVENTION

Briefly summarized, the present invention relates to a gas detector having a heated electrode sensing device for sensing the presence of one or more predetermined gas and one or more control loops for controlling the operation of the sensing device. Broadly defined, the gas detector according to one aspect of the present invention is operative in conjunction with a power source and includes: a detection circuit, the detection circuit including a sensing device having first and second electrodes, wherein the first electrode is connected to the power source for heating the first electrode; a temperature controller operatively connectable to the detection circuit for maintaining a temperature of the first electrode at a predetermined magnitude; and a current controller operatively connectable to the detection circuit for maintaining a current in the second electrode at a predetermined magnitude.

In features of this gas detector, the temperature controller is operatively connected to the detection circuit during a first mode of operation, and the current controller is operatively connected to the detection circuit during a second mode of operation; the first mode of operation is a warm-up phase, and the second mode of operation is a normal operation phase; the gas detector has a switch adjustable between at least two positions, wherein in a first switch position the temperature controller is operatively connected to the detection circuit and in a second switch position the current controller is operatively connected to the detection circuit; the position of the switch is determined on the basis of an operating condition of the gas detector; and the sensing device includes a cathode wire, an anode wire at least partly surrounding the cathode wire and having opposing ends, a pair of supply contacts electrically connected to respective ends of the anode wire, a pair of temperature sense contacts electrically connected to respective ends of the anode wire, and a cathode contact electrically connected to an end of the cathode wire.

The present invention also includes a method of controlling the operation of a gas sensing device, the gas sensing device for indicating the presence of a gas of a predetermined type, wherein the method includes the steps of: adjustably heating the gas sensing device; generating a bias current; controlling the temperature of the heated gas sensing device on the basis of at least one operating condition of the sensing device; and controlling the bias current generated by the heated gas sensing device on the basis of at least one operating condition of the sensing device.

In features of this method, the temperature controlling step includes the step of maintaining the temperature of the heated gas sensing device at a predetermined absolute temperature; the method further comprises the step of moving the sensing device into the presence of a gas of a predetermined type, and the bias current controlling step includes the step of maintaining the magnitude of the bias current at a generally constant level during the moving step; generating a signal at least partially representative of the temperature of the sensing device and monitoring the signal for an indication of the presence of at least one predetermined gas; the steps of controlling the temperature of the heated gas sensing device and controlling the bias current generated by the heated gas sensing device occur sequentially; and the transition from one of the controlling steps to the other occurs on the basis of at least one operating condition of the sensing device.

In another aspect of the present invention, a controller for controlling the operation of a gas detector, the gas detector for indicating the presence of a gas of a predetermined type and having a heated gas sensing device generating a bias current, includes: a temperature control loop for controlling the temperature of the heated gas sensing device on the basis of at least one operating condition of the sensing device; and a bias current control loop for controlling the bias current generated by the heated gas sensing device on the basis of at least one operating condition of the sensing device.

In features of this aspect, the temperature control loop is operatively connected to a detection circuit during a first mode of operation, which may be a warm-up phase, and the bias current control loop is operatively connected to the detection circuit during a second mode of operation, which may be a normal operation phase; the controller has a switch adjustable between at least a first switch position in which the temperature control loop is operatively connected to a detection circuit and a second switch position in which the bias current control loop is operatively connected to the detection circuit; the position of the switch is determined on the basis of an operating condition of the gas detector; the sensing device includes a cathode wire, an anode wire at least partly surrounding the cathode wire and having opposing ends, a pair of supply contacts electrically connected to respective ends of the anode wire, a pair of temperature sense contacts electrically connected to respective ends of the anode wire, and a cathode contact electrically connected to an end of the cathode wire, and the temperature control loop is electrically connected to the temperature sense contacts; and an output of the bias current control loop is electrically connected to an input of the temperature control loop.

The present invention also includes a method of controlling a gas detector for sensing the presence of at least one predetermined gas, the gas detector having a heated first electrode and a second electrode, wherein the method includes the steps of: heating the first electrode to a predetermined absolute temperature; upon reaching the predetermined absolute temperature, placing the electrodes in a test location; upon being exposed to one of the predetermined gases, generating an increased current in the second electrode; and maintaining the first electrode at substantially the predetermined absolute temperature while placing the electrodes in the test location and while generating the increased current.

In features of this method, the method further includes the steps of selecting the predetermined absolute temperature and, while the detector is being operated, providing an indication of the predetermined absolute temperature to the gas detector; the step of providing an indication of the predetermined absolute temperature includes the step of predefining the predetermined absolute temperature during manufacturing; the step of providing an indication of the predetermined absolute temperature includes the step of entering the predetermined absolute temperature into the gas detector; the amount of heat applied to the first electrode is dependent on a duty cycle, and the step of maintaining the first electrode at substantially the predetermined absolute temperature includes the step of adjusting the duty cycle; the method further includes the step of monitoring the actual temperature of the first electrode, and the step of maintaining the first electrode at substantially the predetermined absolute temperature includes the steps of reducing the temperature of the first electrode upon determining that the actual temperature exceeds the predetermined absolute temperature and raising the temperature of the first electrode upon determining that the actual temperature is below the predetermined absolute temperature.

The present invention also includes a method of controlling a heated electrode gas detector for sensing the presence of at least one predetermined gas, the gas detector having first and second electrodes, wherein the method includes the steps of: selecting a preferred absolute temperature; providing an indication of the selected preferred absolute temperature to the gas detector; adjustably heating the first electrode; upon being exposed to one of the predetermined gases, generating an increased current in the second electrode; monitoring the temperature of the first electrode while the increased current is being generated; comparing the monitored temperature to the selected preferred absolute temperature; and varying the heating of the first electrode on the basis of the outcome of the comparing step.

In features of this method, the step of providing an indication of the selected preferred absolute temperature includes the step of entering a value corresponding to the selected preferred absolute temperature into the gas detector; the step of providing an indication of the selected preferred absolute temperature includes the step of predefining the selected predetermined absolute temperature to the gas detector during manufacturing; the step of varying the heating of the first electrode includes the steps of reducing the temperature of the first electrode upon determining that the monitored temperature exceeds the selected preferred absolute temperature and raising the temperature of the first electrode upon determining that the monitored temperature is below the selected preferred absolute temperature; at least the monitoring, comparing and varying steps are repeated substantially continuously during operation of the gas detector; the selected preferred absolute temperature is a first preferred absolute temperature, and the method further includes the steps of selecting a second preferred absolute temperature, providing an indication of the second selected preferred absolute temperature to the gas detector, adjustably heating the first electrode, generating an increased current in the second electrode upon being exposed to any of the predetermined gases, monitoring the temperature of the first electrode while the increased current is being generated, comparing the monitored temperature to the second selected preferred absolute temperature, and varying the heating of the first electrode on the basis of the outcome of the comparing step.

The present invention also includes a method for sensing the presence of at least one predetermined gas at a sensing device having first and second electrodes, wherein the method includes the steps of: heating the first electrode; generating, at the second electrode, a bias current; moving the sensing device into the presence of one of the predetermined gases; maintaining the magnitude of the bias current at a generally constant level during the moving step; generating a signal at least partially representative of the temperature of the sensing device; and monitoring the temperature signal for an indication of the presence of at least one predetermined gas.

In features of this method, the presence of a predetermined gas is indicated by a decrease in temperature; the bias current is a first signal, and the temperature signal is a second signal; the first electrode includes at least two ends, and the generating step includes generating the temperature signal at one or more of the ends of the first electrode; the step of generating the bias current includes the step of generating the bias current according to a duty cycle, and the step of maintaining the magnitude of the bias current at a generally constant level includes maintaining the magnitude of the bias current at a generally constant level according to the value of the duty cycle.

The present invention also includes a method for sensing the presence of at least one predetermined gas at a sensing device having first and second electrodes, wherein the method includes the steps of: heating the first electrode; generating, at the second electrode, a bias current; generating a first signal at least partially representative of the magnitude of the bias current, the magnitude of the bias current being a first operating condition; generating a second signal at least partially representative of a second operating condition; maintaining the magnitude of the bias current at a generally constant level on the basis of the first signal; and monitoring the second signal for an indication of the presence of at least one predetermined gas.

In features of this method, the second operating condition is a temperature of the sensing device; the presence of a predetermined gas is indicated by a decrease in temperature; the first electrode includes at least two ends, and the step of generating a second signal includes generating the second signal at one or more of the ends of the first electrode; the method further includes the step of moving the sensing device into the presence of one of the predetermined gases, and the maintaining step includes maintaining the magnitude of the bias current at a generally constant level during the moving step; the step of generating the bias current includes the step of generating the bias current according to a duty cycle, and the step of maintaining the magnitude of the bias current at a generally constant level includes maintaining the magnitude of the bias current at a generally constant level according to the value of the duty cycle.

The present invention also includes a method of estimating the remaining useful life of a heated electrode gas detector for sensing the presence of at least one predetermined gas, the gas detector having first and second electrodes, wherein the method includes the steps of: adjustably heating the first electrode to maintain a current in the second electrode of a predetermined magnitude, the magnitude of the current being at least partly dependent upon the temperature of the first electrode; while heating the first electrode, determining information at least partly representative of the operating temperature of the gas detector; comparing the operating temperature information to information representative of a maximum operating temperature; and determining the remaining useful life of the gas detector on the basis of the comparison.

In features of this method, the information at least partly representative of the operating temperature of the gas detector and the information representative of the maximum operating temperature are both particular values; the determining information step includes sensing the actual operating temperature of the gas detector; the information at least partly representative of the operating temperature of the gas detector and the information representative of the maximum operating temperature are both particular temperature values; the information at least partly representative of the operating temperature of the gas detector is a particular duty cycle value, which corresponds to the operating temperature of the gas detector; the step of comparing the temperatures includes subtracting the operating temperature value from the maximum operating temperature value; the step of determining the remaining useful life includes determining the remaining useful life of the gas detector as a function of the difference between the operating temperature value and the maximum operating temperature value; the method further includes the step of predetermining the maximum operating temperature; the step of predetermining the maximum operating temperature is done empirically; and the maximum operating temperature is a maximum safe operating temperature of the gas detector and/or the maximum operating temperature is a maximum effective operating temperature of the gas detector.

In another aspect of the present invention, a gas detector for sensing the presence of at least one predetermined gas and operative in conjunction with a power source, includes an anode/cathode assembly coated with a ceramic material, the anode/cathode assembly having a cathode wire and an anode wire at least partly surrounding the cathode wire, wherein the anode wire has opposing ends and wherein one of the anode wire ends is electrically connected to the power source; a pair of supply contacts electrically connected to respective ends of the anode wire; a pair of temperature sense contacts electrically connected to respective ends of the anode wire; a cathode contact electrically connected to an end of the cathode wire; and a temperature-sensing circuit electrically connected to at least one of the temperature sense contacts for monitoring the temperature of the anode/cathode assembly.

In features of this aspect, the power source is electrically connected to at least one of the supply contacts; the gas detector has a bias current-sensing circuit electrically connected to the cathode contact; the gas detector has a current source electrically connected to at least one of the supply contacts; and the gas detector has a switch for bypassing the current source.

The present invention also includes a method of making a sensing device for a heated electrode gas detector, the method including the steps of: inserting a cathode wire into an uncoated anode coil to form an electrode assembly; after inserting the cathode wire into the uncoated anode coil, coating the electrode assembly with a ceramic material; and firing the coated electrode assembly.

In features of this method, the inserting step includes inserting an uncoated cathode wire into the uncoated anode coil to form the electrode assembly; the firing step is accomplished by applying a heating current to the anode coil; the method includes the step of biasing the coated electrode assembly by applying a biasing voltage to the electrode assembly; and the steps of firing and biasing are carried out substantially entirely simultaneously.

The present invention also includes a method of making a sensing device for a heated electrode gas detector, the method including the steps of: inserting a cathode wire into an anode coil to form an electrode assembly; coating at least part of the cathode wire and at least part of the anode coil with a ceramic material to form an unfired electrode assembly; and biasing the unfired electrode assembly to form a depletion region.

In features of this method, the biasing step includes biasing the unfired electrode assembly by applying a biasing voltage to the anode coil; the method further includes the step of firing the unfired electrode assembly by applying a heating current to the anode coil; and the steps of firing and biasing are carried out substantially entirely simultaneously; the firing and biasing steps are completed within one hour.

The present invention also includes a method of efficiently preparing a heated electrode refrigerant detector for use, the detector including a sensing device, wherein the method includes the steps of: determining a first temperature, the first temperature being a desired sensing device operating temperature; determining a second temperature, the second temperature being higher than the first temperature; gradually raising the actual temperature of the sensing device from a third temperature until the second temperature is reached, wherein the third temperature is substantially less than the first temperature; and after reaching the second temperature, lowering the actual temperature of the sensing device until the first temperature is reached.

In features of this method, the second temperature is generally equal to the maximum sustainable operating temperature of the sensing device; and the third temperature is the ambient temperature of the sensing device before the sensing device is heated.

The present invention also includes a method of preparing a heated electrode refrigerant detector for use, the detector including a sensing device, wherein the method includes the steps of: maintaining the actual temperature of the sensing device at a first temperature; while maintaining the actual temperature of the sensing device at the first temperature, generating a bias current, the bias current decreasing in magnitude over time; monitoring the bias current; and on the basis of the monitored bias current, reducing the actual temperature of the sensing device to a second temperature which is a desired sensing device operating temperature.

In features of this method, the first temperature is generally equal to the maximum safe operating temperature of the sensing device; the temperature reducing step is executed on the basis of the negative slope of the monitored bias current over time being less than a predetermined value; and the temperature reduction is effected by reducing the magnitude of the bias current to a desired operating level.

The present invention also includes a method of re-polarizing a heated electrode refrigerant detector having a sensing device operable at an operating temperature, the method including the steps of: elevating the temperature of the sensing device above the operating temperature until the sensing device is substantially re-polarized; and decreasing the temperature of the sensing device to the operating temperature.

In features of this method, the method further includes the step of monitoring the magnitude of a bias current generated by the sensing device, and the initiation of the step of decreasing the temperature of the sensing device is dependent at least partly upon the magnitude of the bias current; and the method further includes the step of monitoring the amount of time for which the temperature of the sensing device is elevated above operating temperature, and the initiation of the step of decreasing the temperature of the sensing device is dependent at least partly upon the amount of time.

The present invention also includes a method of efficiently preparing a heated electrode refrigerant detector, having a sensing device, for use, the method including the steps of: turning the detector on; increasing the actual temperature of the sensing device at a first rate of increase; monitoring at least one operating condition of the sensing device; and on the basis of an operating condition of the sensing device, increasing the actual temperature of the sensing device at a second rate of increase until a desired sensing device operating temperature is reached.

In features of this method, the sensing device is capable of generating a bias current, and the step of monitoring an operation condition includes monitoring the bias current; the step of increasing at a second rate occurs on the basis of the magnitude of the bias current being substantially equal to zero; the step of monitoring an operation condition includes monitoring absorbed moisture in the sensing device; the step of increasing at a second rate occurs on the basis of the substantially all of the initial quantity of absorbed moisture being evaporated; the step of monitoring absorbed moisture in the sensing device includes determining whether any absorbed moisture is present; the first rate of increase may be between 50 and 100 degrees Celsius per second; and the second rate of increase may be between 500 and 2000 degrees Celsius per second.

The present invention also includes a method of operating a heated electrode refrigerant detector, the method including the steps of: defining a sequence of desired temperature values; and adjusting the temperature of the detector according to the defined sequence.

In features of this method, the step of adjusting the temperature includes, for each desired temperature value in the sequence, the steps of determining the next desired temperature value in the sequence, controlling the temperature of the detector to effect the desired temperature value, monitoring the temperature of the detector to determine if the desired temperature value has been reached, and repeating the controlling and monitoring steps until the desired temperature value has been reached; the method includes the step of storing the desired temperature values in a memory; and the sequence of desired temperature values is selected to create a ramp function of temperature versus time.

BRIEF DESCRIPTION OF THE DRAWINGS

Further features, embodiments, and advantages of the present invention will become apparent from the following detailed description with reference to the drawings, wherein.

DETAILED DESCRIPTION OF THE PREFERRED EMBODIMENTS

Figure 2:
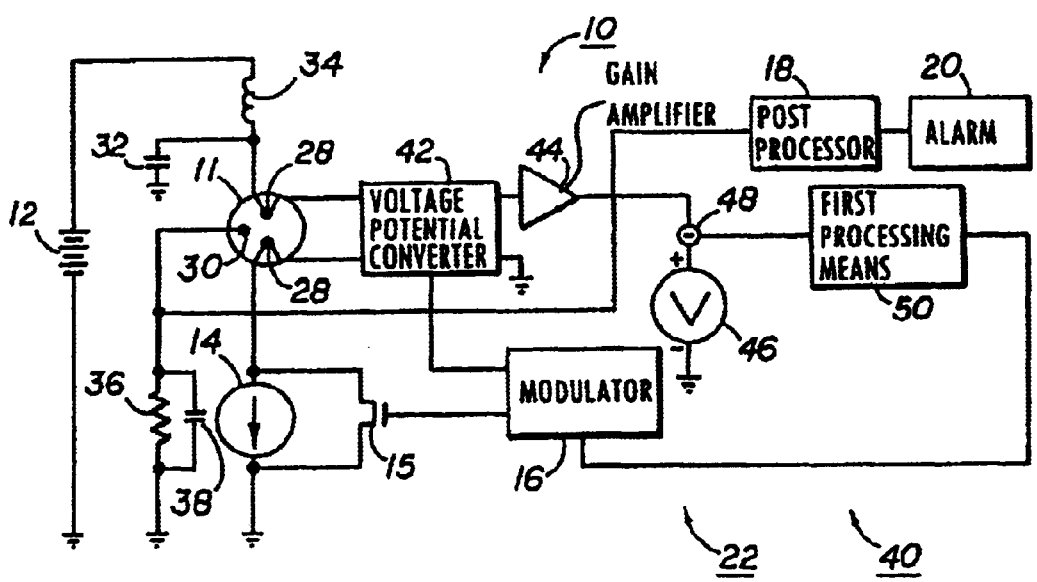
FIG. 2 is a schematic diagram of a first preferred embodiment of a heated electrode refrigerant detector according to the present invention.
Figure 4:
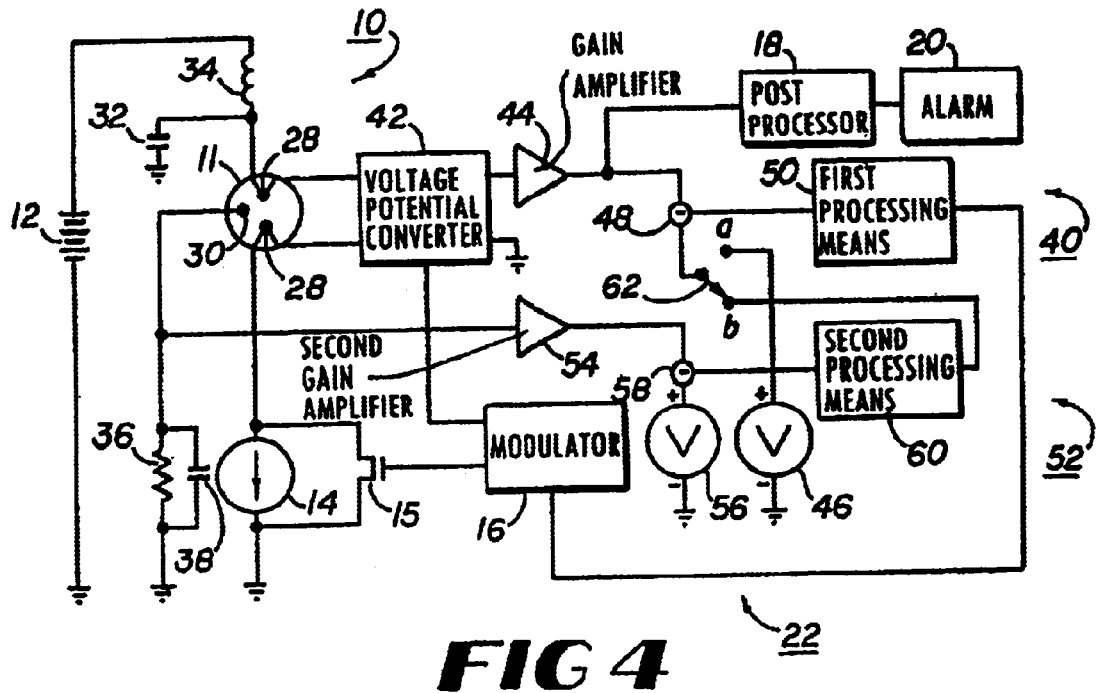
FIG. 4 is a schematic diagram of a third preferred embodiment of the heated electrode refrigerant detector of the present invention.
Figure 3:
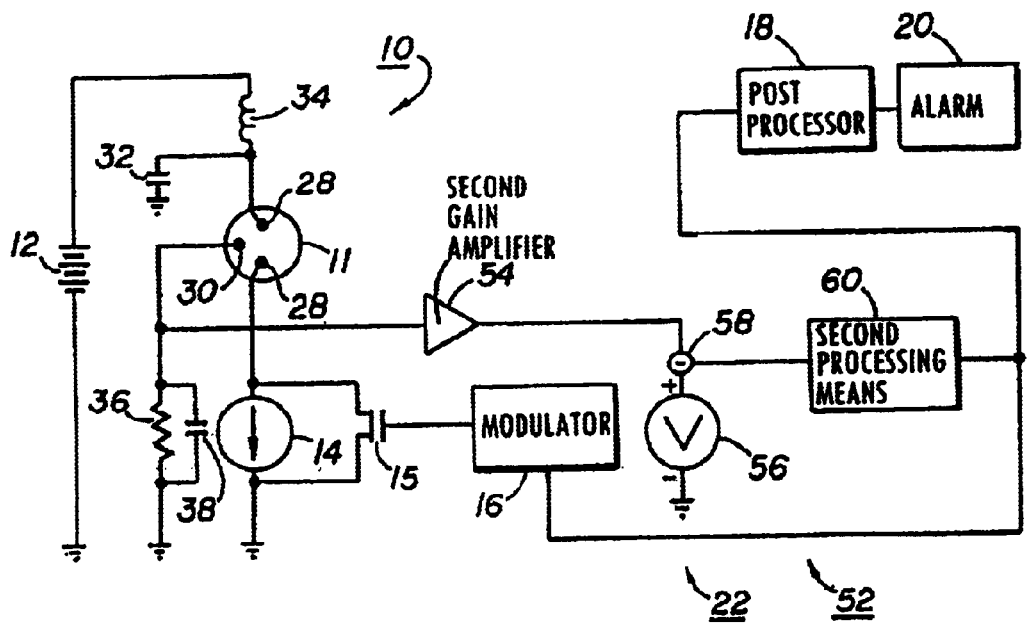
FIG. 3 is a schematic diagram of a second preferred embodiment of the heated electrode refrigerant detector of the present invention.

Referring now to the drawings, in which like numerals represent like components throughout the several views, an improved heated electrode refrigerant detector 5 having one or more control loop, in accordance with the preferred embodiments of the present invention, will now be shown and described. FIGS. 2–4 are schematic diagrams of first, second and third preferred embodiments of the improved heated electrode refrigerant detector 5 of the present invention.

In each preferred embodiment, the heated electrode refrigerant detector 5 of the present invention comprises a primary detection circuit 10, a post-processor 18 for post-processing one or more signals, a leak detection indicator and alarm 20 and at least one control loop 22. The primary detection circuit 10 includes a sensing device 11, a battery power supply 12, a current source 14, a switch 15 for bypassing the current source 14, a modulator 16 for modulating the switch 15 according to a desired duty cycle determined by one or more of the control loops 22, and a number of basic circuitry components, including first and second capacitors 32, 38, a resistor 36 and an inductor 34.

Figure 1:
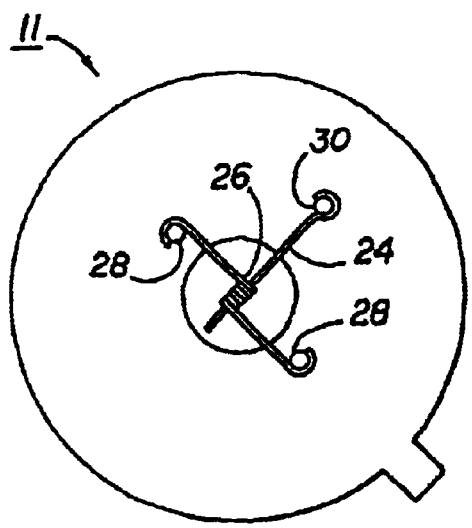
FIG. 1 is a detailed diagrammatic view of a prior art sensing device for use in various embodiments of the heated electrode refrigerant detectors of the present invention.
Figure 6:
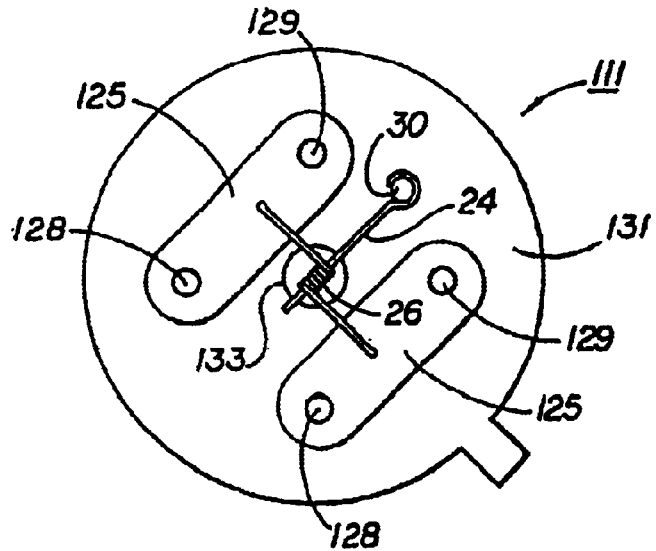
FIG. 6 is a detailed diagrammatic view of an improved sensing device suitable for use in the primary detection circuits of FIGS. 2–4.

The sensing device 11 may be any conventional heated electrode refrigerant sensing device such as the one previously described and illustrated in FIG. 1, or may alternatively be an improved sensing device such as the one described in conjunction with FIG. 6. Further, in an improved method of making the sensing device 11 shown in FIG. 1 or the improved sensing device 111 shown in FIG. 6, an uncoated cathode wire 24 may be inserted into the uncoated anode coil 26, with the combination then being coated with one or two coatings of the ceramic material described previously. The unfired anode/cathode assembly may then be mounted within the housing, which may be a standard TO-5 can. The sensing device 11 is then energized, thus firing and biasing the sensing device 11 simultaneously in a relatively short period of time. It has been found that satisfactory performance in terms of sensitivity and repeatability may be achieved in as little as thirty minutes, thus reducing assembly time dramatically.

As shown, the sensing device 11 may be electrically connected to the rest of the primary detection circuit 10 via its anode contacts 28 and its cathode contact 30. As is well known in the art, when thus installed in a suitable circuit, such as the primary detection circuit 10 of the present invention, a bias current is generated at the cathode contact 30. The magnitude of the bias current is dependent on the average potential difference between the voltage drop across the anode coil and the cathode voltage, the temperature of the sensing device 11, the length of time the sensing device 11 has been operating, the ambient concentration of halogenated molecules surrounding the sensing device 11, and the history of the sensing device's exposure to halogenated molecules during all of its previous usage. Thus, after "burning in" the sensing device 11, subsequent exposure of the sensing device 11 to reactive gases like halogen, while the device 11 is being heated, causes ions to flow from the anode 26 to the cathode 24, causing an increase in the bias current. This characteristic may therefore be used as an indicator of the presence or absence of halogenated molecules at the sensing device 11.

The battery power supply 12 may be any readily available battery device which in a typical embodiment may supply an unregulated voltage in the range of 4 to 8 VDC. The switch may be a transistor or other suitable device capable of propagating a current through the anode coil 26 of the sensing device 11 at a suitable input frequency and duty cycle, which as described herein may be 20 kHz and less than 10% respectively. At its typical operating temperature of 600° C. to 1000° C., the anode coil 26 has an effective resistance of approximately 1 ohm. Thus, during the brief portion of each cycle when the switch 15 is "on," a current is generated through the anode coil 26 of approximately 4A to 8A. Because of the large magnitude of this current, a first capacitor 32 and an inductor 34 are provided on the power supply side of the sensing device 11 to filter the current spikes of generally short duration (typically 1.5 $\mu$sec to 4.0 $\mu$sec) which would otherwise present significant noise on the power supply.

The current source 14 provides a fixed current of much smaller magnitude than that which is generated through the anode coil 26 while the switch 15 is on. In a suitable embodiment, the current source may supply a current of 10 mA. During that portion of each cycle when the switch 15 is "off,"a current of approximately 10 mA is thus generated through the anode coil 26. The voltage drop across the anode coil 26 while the switch is off is directly proportional to the effective resistance of the anode coil 26. Because this resistance is a function of the temperature of the coil 26, which increases in approximately linear fashion, and because the current through the coil 26 is constant while the switch 15 is "off," the magnitude of the voltage drop across the anode coil 26 while the switch 15 is "off" thus provides a direct indication of the absolute temperature of the sensor.

Also, while the switch 15 is "off", the anode voltage is very high with respect to the cathode voltage, and thus the potential difference between the anode voltage and the cathode voltage is nearly equal to the voltage supplied by the batter power supply 12. Because the switch 15 is "off" over 90% of the time, the average difference between the anode and cathode voltages is much larger than in prior art solutions. This results in a greater bias current, and therefore, greater sensitivity at lower sensing device 11 temperatures.

The resistor 36 and the second capacitor 38 are connected to the cathode contact 30 on the sensing device 11. Thus, when a bias current is generated at the cathode contact 30, a voltage which is proportional to the bias current is generated across the resistor 36 and filtered by the second capacitor 38. In a typical embodiment, the resistor 36 may have a value of 100 KOhm, and the second capacitor 38 may have a value of 0.1 $\mu F$. Thus, when the temperature of the sensing device 11 remains relatively constant, bringing the sensing device 11 into the presence of halogen molecules would cause a noticeable change in the voltage level across the resistor 36.

As described hereinbelow, a signal corresponding to the bias current voltage level is one of the one or more signals which may be provided to the post-processor 18 in order to provide information about the presence or absence of halogen molecules at the sensing device 11 to the user. Another signal which may be provided to the post-processor 18 is a signal corresponding to the temperature of the sensing device 11 during the "off" periods of the switch 15. Yet another signal which may be provided to the post-processor 18 is the duty cycle set-point signal which is used to set the duty cycle at which the modulator 16 is operating. The post-processor 18 is capable of detecting or recognizing certain predetermined conditions at the sensing device 11 and controlling one or more leak detection indicators or alarms 20 to inform the user of the presence of a refrigerant leak.

In the first embodiment of the present invention, shown in FIG. 2, the control loops 22 include only a temperature control loop 40. The temperature control loop 40, which is preferably implemented digitally using a microprocessor and appropriate code, but may also be implemented using discrete components, includes a voltage potential converter 42, first gain amplifier 44, a temperature input means 46, a first subtractor 48 and a first processing means 50. The voltage potential converter 42 is a switched-capacitor synchronous differential-to-single-ended converter which converts the differential temperature signal present at the anode contacts 28 into a single-ended signal. The voltage potential converter 42 also receives a synchronized input from the modulator 16 so that only the voltage present at the anode contacts 28 during the "off" time of the switch 15 is converted. The output of the voltage potential converter 42 is connected to the first gain amplifier 44, which is a non-inverting amplifier of well known construction and may have a gain of 150.

The output of the first gain amplifier 44 is connected to one input of the first subtractor 48, while the other input of the first subtractor 48 is connected to the temperature input means 46. The temperature input means 46 may be any suitable means for inputting voltage level data corresponding to a particular desired operating temperature for the sensing device 11. If a microprocessor is utilized, then the preferred temperature input means 46 would be either a preprogrammed set-point or a pre-defined temperature vs. time profile, with the former being used for fixed temperature operation, and the latter for the preferred warm-up procedure described herein and/or for normal operation. Either the preprogrammed set-point or the temperature-time profile could be programmed into a microprocessor in order to eliminate user intervention. Additionally, in the microprocessor-controlled system, it should be clear that the input from the temperature input means 46 and the output of the first gain amplifier 44 may both be digitized, and so the values processed by the first subtractor 48 may be digitized values rather than actual voltages.

If the temperature control loop 40 is instead implemented in discrete components, then the temperature input means 46 preferably includes a keypad for numerically inputting a particular desired temperature which may then be automatically converted to a corresponding voltage level, but it should be clear that other devices may be used to input a particular number, and that alternatively a user could input the voltage level corresponding to a particular temperature directly without any need for conversion. Alternatively, the temperature input means 46 could include an adjustment means for adjusting the voltage level relative to its current value rather than entering the desired voltage level directly. Regardless of the method or apparatus utilized to input the desired temperature set point, the first subtractor 48 determines the difference between the signal from the output of the first gain amplifier 44 and the signal from temperature input means 46 and makes the difference available at its output.

The output of the first subtractor 48 is connected to the first processing means 50, both of which may easily be constructed by one of ordinary skill in the art of signal processing methods and apparatuses. The first processing means 50, which is an analog or digital filter whose coefficients may be determined empirically by one of ordinary skill, may be utilized to amplify and phase-compensate the signal from the first subtractor 48. The output of the first processing means 50 is connected to the input of the modulator 16 to provide a duty cycle set signal to the modulator 16. The modulator 16 is a pulse width modulator which utilizes an oscillator to provide a reliable output signal at a uniform frequency with a controllable duty cycle. The value of the duty cycle is dependent upon the output from the first processing means 50. In an exemplary embodiment, the output signal from the modulator 16 has a frequency of approximately 20 kHz and a duty cycle ranging from approximately 3% to 8%. The output from the modulator 16 is connected to the switch 15 in order to modulate the current generated through the anode coil 26.

In operation, the user turns the refrigerant detector 5 on and a desired temperature is provided to the refrigerant detector 5 in one of the manners described above using the temperature input means 46. The temperature control loop 40 supplies a pulse width modulation signal to the switch 15 at a set duty cycle. During the "off" portion of the duty cycle, the temperature control loop 40 converts and amplifies the voltage potential present at the anode contacts 28 and subtracts that signal from the desired set point signal provided from the temperature input means 46. The resulting error signal is amplified and phase-compensated by the first processing means 50 in order to optimize settling time, overshoot and ringing. The output of the first processing means 50 is a duty cycle set signal which is provided as an input to the modulator 16. The modulator 16 then adjusts the duty-cycle of the modulation to counteract against any rise or drop in the temperature of the sensing device. When the measured temperature of the sensing device 11 is lower than the desired temperature, then the duty cycle set signal represents an instruction to the modulator 16 to increase the duty cycle thus leaving the switch 15 "on" for a greater proportion of the period of each cycle and allowing the anode coil 26 to be heated by the battery power supply 12 a greater amount of the time. The effect of this is to raise the temperature of the sensing device 11 to the desired temperature input using the temperature input means 26. On the other hand, when the measured temperature of the sensing device 11 is higher than the desired temperature, then the duty cycle set signal represents an instruction to the modulator 16 to decrease the duty cycle, thus leaving the switch 15 "on" for a lesser proportion of the period of each cycle and allowing the anode coil 26 to be heated by the battery power supply 12 a lesser amount of the time. The effect of this is to lower the temperature of the sensing device 11 to the desired temperature which was input using the temperature input means 46. By constantly monitoring the actual temperature of the sensing device 11 and adjusting the amount of applied power accordingly, the temperature of the sensing device 11 may be held substantially constant.

Once the refrigerant detector 5 is operative, the user may utilize it to detect the presence of halogen molecules and accordingly, to identify a refrigerant leak. To detect a leak, the refrigerant detector 5 may first be reset in a location which is known to be free of halogen molecules. The refrigerant detector 5 may then be moved to the desired test location. If the sensing device 11 is moved into the presence of halogen molecules, the bias current will correspondingly increase, resulting in a corresponding increase in the voltage across the resistor 36. This increase in the magnitude of the bias current from the sensing device 11 is then detected by the post-processor 18 and the leak detection indicators and alarms 20 are utilized to inform the user of the presence of a leak.

Although a bias current increase may also be caused by an increase in the temperature of the sensing device 11, which commonly occurs when prior art refrigerant sensors are moved from a cooler area to a warmer one, the temperature of the sensing device 11 of the present invention is maintained at a constant controllable temperature by the temperature control loop 40. False readings caused by an increase in bias current generated as a result of a higher sensing device temperature are thus avoided, as are false readings caused by fluctuations in the battery power supply 12. As a result, an increase in the bias current may more dependably be interpreted by the refrigerant detector 5 as indicating the presence of halogen molecules rather than being a false reading.

In a second embodiment of the present invention, shown in FIG. 3, the control loops 22 include only a bias current control loop 52. The bias current control loop 52, which may also be implemented by either digital (microprocessor and code) or analog (discrete components) means, includes a second gain amplifier 54, a bias current input means 56, a second subtractor 58 and a second processing means 60. The input of the second gain amplifier 54, which is a non-inverting amplifier of well known construction and may have a gain of 16, is connected to the cathode contact 30 and carries a voltage level proportional to the bias current of the sensing device 11. The output of the second gain amplifier 54 is connected to one input of the second subtractor 58, while the other input of the second subtractor 58 is connected to the bias current input means 56. The bias current input means 56 may be any suitable means for inputting a voltage level corresponding to a particular desired operating bias current magnitude. Empirical study has determined that increasing the bias current results in greater sensitivity, but substantially reduces the life of the sensing device 11. In a preferred embodiment, these factors are balanced by maintaining the bias current in the range from 0.4 $\mu$A to 0.8 $\mu$A, which corresponds to a voltage range of 40 mV to 80 mV when the resistor 36 has a resistance of 100 KOhm. If a microprocessor is utilized, then the preferred bias current input means 56 may be a pre-programmed set-point which could be programmed into the microprocessor in order to eliminate user interruption. Moreover, a plurality of pre-programmed set-points may be provided for different purposes, and the bias current input means 56 may include a selection means for selecting the preferred setting, wherein the plurality of set-points may include a first set-point by which sensitivity is maximized, a second set-point by which sensing device life is maximized, and a third set-point by which the above-described compromise between sensitivity and sensing device life is reached. Additionally, in the microprocessor-controlled system, it should be clear that the input from the bias current input means 56 and the output of the second gain amplifier 54 may both be digitized, and so the values processed by the second subtractor 58 may be digitized values rather than actual voltages. If the bias current control loop 52 is instead implemented in discrete components, the bias current input means 56 preferably includes a keypad for numerically inputting a particular bias current which may then be automatically converted to a corresponding voltage level, but it should be clear that other devices may be used to input a particular number, and that alternatively a user could input the voltage level corresponding to a particular bias current magnitude directly without any need for conversion. Alternatively, the bias current input means 56 could include an adjustment means for adjusting the voltage level relative to its current value rather than entering the desired voltage level directly.

Regardless of the method or apparatus utilized to input the desired bias current set point, the second subtractor 58 determines the difference between the signal from the output of the second gain amplifier 54 and the signal from bias current input means 56 and makes the difference available at its output. The output of the second subtractor 58 is connected to the second processing means 60, both of which may easily be constructed by one of ordinary skill in the art of signal processing methods and apparatuses. Like the first processing means 50, the second processing means 60 is an analog or digital filter whose coefficients may be determined empirically by one of ordinary skill and may be utilized to amplify and phase-compensate the signal from the second subtractor 58. The output of the second processing means 60 is connected to the input of the modulator 16 to provide a duty cycle set signal to the modulator 16, which may be identical to the pulse width modulator described with regard to the first preferred embodiment. As with the first preferred embodiment, the output from the modulator 16 is connected to the switch 15 in order to modulate the current generated through the anode coil 26 at a frequency of approximately 20 kHz and a duty cycle ranging from approximately 3% to 8%.

In operation, the user turns the refrigerant detector 5 on and a bias current of a desired magnitude is provided to the refrigerant detector 5 in one of the manners described above using the bias current input means 56. The bias current control loop 52 supplies a pulse width modulation signal to the switch 15 at a set duty cycle. The bias current control loop 52 converts and amplifies the voltage potential across the resistor 36 and subtracts that signal from the desired set point signal provided from the bias current input means 56.

The resulting error signal is amplified and phase-compensated by the second processing means 60 in order to optimize settling time, overshoot and ringing. The output of the second processing means 60 is a duty cycle set signal which is provided as an input to the modulator 16. The modulator 16 then adjusts the duty-cycle of the modulation to raise or lower the amount of heating applied to the sensing device 11 as described with regard to the temperature control loop 40. Because the magnitude of the bias current is directly related to the temperature of the sensing device 11, a rise or drop in the temperature of the sensing device 11 results in a corresponding respective rise or drop in the magnitude of the bias current. Thus, any change in the magnitude of the bias current is detected by the bias current control loop 52 and counteracted by a corresponding adjustment to the temperature of the sensing device 11 to bring the bias current back to the specified level. Because this process occurs continuously, the bias current from the sensing device 11 is always maintained reasonably close to the set point regardless of any external influence or conditions, including the presence or absence of halogen molecules at the sensing device 11.

Once the refrigerant detector 5 is operative, the user may utilize it to detect the presence of halogen molecules and accordingly, to identify a refrigerant leak. To detect a leak, the refrigerant detector 5 may first be reset in a location which is known to be free of halogen molecules. The refrigerant detector 5 may then be moved to the desired test location. If the sensing device 11 is moved into the presence of halogen molecules, the bias current will momentarily start to increase, resulting in a corresponding initial increase in the voltage across the resistor 36. In reaction, the bias current control loop 52 will adjust the duty cycle to lower the temperature of the sensing device 11, thus effecting a corresponding decrease in the magnitude of the bias current in order to effectively keep the bias current constant. In this embodiment, the presence of halogen molecules may thus be indicated by a rapid reduction in the temperature of the sensing device 11 rather than by an increase in the bias current. However, in order to avoid having to monitor the temperatures of the sensing device 11 directly, the post-processor 18 may be adapted to receive information related to the duty cycle of the modulator 16, and to control the leak detection indicators and alarms 20 on the basis of that information rather than on the basis of the temperature of the sending device 11. This is because the temperature of the sending device 11 is related to the power applied to the sensing device 11, and that power is directly related to the value of the duty cycle. Thus, any change to the temperature of the sensing device 11 may be seen first as a change in the duty cycle of the modulator 16. Thus, the occurrence of a rapid reduction in the duty cycle of the sensing device 11 may be detected by the post-processor 18 and the leak detection indicators and alarms 20 are utilized to inform the user of the presence of a leak. It should be obvious to one of ordinary skill, however, that the post-processor 18 may alternatively be adapted to receive information related directly to the temperature of the sensing device 11, in which case a decrease in the temperature thus directly indicates the presence of halogen molecules at the sensing device 11.

In a further feature of the present invention, a method is also provided for determining the remaining useful life of a detector 5 having a bias current control loop 52. Because over time, the bias current generated by the sensing device 11 would naturally tend to decrease as the sensing device 11 is used up, the temperature must regularly be increased in order to compensate for this natural decrease. However, every sensing device 11 has a maximum safe operating temperature above which it cannot be safely operated without significantly increasing the risk of damage to the detector 5 and injury to the user. This maximum safe operating temperature may preferably be determined empirically by the manufacturer and provided to the user either in written technical information or via the microprocessor, if one is used. The maximum safe operating temperature may then be utilized by the user to estimate the remaining useful life of the detector 5 as follows. As the anode 26 is variably heated to maintain a constant bias current in the cathode 24, the actual operating temperature of the sensing device 11 may be sensed either directly or derived from the actual duty cycle frequency and compared to the maximum safe operating temperature. The remaining useful life of the detector 5 may then be determined as a function of the difference between the actual operating temperature and the maximum safe operating temperature. If a microprocessor is utilized, then the remaining useful life may be automatically provided to the user in terms of time, but it should be obvious that a simple function may be used to instead convert the temperature differential to a period of time manually. It should also be obvious that a graduated series of indications of remaining useful life may be provided to the user, such as through the use of a green LED being lit when a minimum useful life remains, a yellow LED being lit when the useful life is almost depleted, and a red LED being lit when the useful life has been reached. It should also be obvious that the remaining useful life may be determined as the difference between the actual operating temperature and a buffered maximum effective operating temperature, wherein the maximum effective operating temperature is lower than the maximum safe operating temperature and is established to allow the temperature of the sensing device 11 to be temporarily increased during operation in order to compensate for significant changes in ambient conditions without exceeding the maximum safe operating temperature. The maximum effective operating temperature may then be interpreted as the maximum temperature above which safe operation of the detector 5 may not be guaranteed under all operating conditions.

In a third embodiment of the present invention, shown in FIG. 4, both a temperature control loop 40 and a bias current control loop 52 are provided. The control loops 40, 52, which may be implemented by either digital (microprocessor and code) or analog (discrete components) means, include a voltage potential converter 42, first and second gain amplifiers 44, 54, temperature and bias current input means 46, 56, first and second subtractors 48, 58, first and second processing means 50, 60 and a controllable switch 62. As described with regard to the first preferred embodiment of the present invention, the voltage potential converter 42 is connected to the anode contacts 28 and the modulator 16 and converts the differential temperature signal present at the anode contacts 28 into a single-ended signal in synchronization with the "off" time of the modulator 16. The output of the voltage potential converter 42 is connected to the first gain amplifier 44, the output of which is connected to the input of the temperature error subtractor 48. As described with regard to the second preferred embodiment of the present invention, the input of the second gain amplifier 54 is connected to the cathode contact 30 of the sensing device 11 and carries a voltage level proportional to the bias current of the sensing device 11. The output of the second gain amplifier 54 is connected to one input of the bias current error subtractor 58, while the other input of the bias current error subtractor 58 is connected to the bias current input means 56 as described previously. The output of the bias current error subtractor 58, which thus carries a signal representing the bias current error, is connected to the second processing means 60.

The controllable switch 62 has one input connected to the output of the second processing means 60 and another input connected to the temperature input means 46. The output of the controllable switch 62 is connected to the input of the temperature error subtractor 48. The controllable switch thus is adaptable to route either the output from the temperature input means 46 to the temperature error subtractor 48 or the output from the second processing means 60 to the temperature error subtractor 48 as desired or on the basis of one or more particular operating condition. As used herein, the term "operating condition" may include, without limitation, a desired or actual temperature, a desired or actual bias current magnitude, a period of time, the amount of moisture in the sensing device 11, and the like. The output of the first subtractor 48 is connected to the first processing means 50 as in the first preferred embodiment, and the output of the first processing means 50 is connected to the input of the modulator 16. Finally, the output of the modulator 16 is connected to the switch 15 in order to modulate the current generated through the anode coil 26.

In operation, the user turns the refrigerant detector 5 on and sets the controllable switch 62 to route the temperature input means 46 to the temperature error subtractor 48. The user may then input one or a series of desired temperatures into the refrigerant sensor 5 using the temperature input means 46. In a preferred method of warming the sensing device 11 up quickly while at the same time minimizing the amount of stress placed thereon, it has been found that the first temperature entered may be zero or its equivalent, followed by a series of successively higher set point values, chosen to create a ramp function, until the sensing device 11 reaches a particular peak temperature. The temperatures in the series may be generated during warm-up using an algorithm based on time, or may be stored in advance in a lookup table or the like. An algorithm suitable for this purpose utilizes as input a starting temperature value, an ending temperature value, and a total ramp time, and repeatedly calculates, as a function of the elapsed time relative to the total ramp time, a series of output temperature values which gradually increase from the defined starting temperature value to the defined ending temperature value along a uniform slope. This combined series of temperatures collectively defines a preferred profile of temperature over time.

Functionally, the temperature changes according to this preferred temperature-time profile are implemented as follows. As each temperature in the temperature-time profile is entered into the temperature control loop 40, an error signal, representing the difference between the actual temperature of the sensing device 11 and the entered temperature, is continually generated by the temperature error subtractor 48, amplified and phase-compensated by the first processing means 50 and provided to the modulator 16, which gradually adjusts the duty cycle of the modulation until the entered temperature is reached.

The amount of time required to ramp the temperature of the sensing device 11 up is dependent upon the amount of time since the detector 5 was last used. When a heated electrode gas detector 5 goes unused for a period of time, the sensing device 11 tends to absorb moisture through hygroscopic action, particularly when the detector goes unused for more than a day. The moisture can be evaporated quickly by energizing the coil 26, thereby raising the temperature. Unfortunately, a rapid rise in temperature, such as a rate of hundreds of degrees Celsius per second, may cause the ceramic portion of the sensing device 11 to crack. Thus, the rate of temperature increase must be limited until the moisture is substantially removed from the sensing device 11, at which time the rate of temperature increase may be raised substantially to minimize the overall warm-up time.

The presence of moisture in the sensing device 11 is indicated by the existence of a bias or leakage current, caused by the conductive effect of the moisture, which may be detected before or after power or heat is applied to the sensing device 11. The evaporation of substantially all of the moisture from the sensing device 11 is indicated by the magnitude of the bias current dropping to zero. Thus, by monitoring the bias current, the temperature control loop 40 may detect the proper time at which to switch from the first rate of temperature increase to the second rate of temperature increase. In an exemplary embodiment, the first rate of temperature increase is selected to be between 50 and 100 degrees Celsius per second, with an exemplary rate of approximately 75 degrees Celsius per second, and the second rate of temperature increase is selected to be between 500 and 2000 degrees Celsius per second, with an exemplary rate of approximately 1000 degrees Celsius per second.

In a preferred embodiment of a method of warming a detector 5 up, the particular peak temperature to which the temperature of the sensing device 11 is raised is in excess of the desired operating temperature, and is preferably chosen to be generally equivalent to the maximum safe operating temperature of the sensing device 11 for reasons which will become apparent below. The sensing device 11 is held at that temperature for a selected period of time until the sensing device 11 is sufficiently warmed up. The period of time for which the sensing device 11 is held above the desired operating temperature depends on a number of factors, the most significant of which is the amount of time, ranging from seconds to months, which the detector 5 has been off. It is believed that an unused sensing device 11 tends to depolarize in an amount which is proportional to the length of time since the last use. Premature use of the detector 5 before the sensing device 11 is re-polarized may exhibit unreliable behavior due to the instability of the temperature of the sensing device 11 or the bias current, depending on whether the bias current control loop 52 or the temperature control loop 40 is currently in operation. The sensing device 11 may be re-polarized by heating it, with the amount of time required to re-polarize being inversely related to the amount of heat which is applied. Thus, the re-polarization time may be minimized by maximizing the temperature to which the sensing device 11 is heated.

Unfortunately, it is possible to over-polarize a sensing device 11, particularly one which has been used only moments before and therefore requires little, if any, re-polarization. This may result in a sharp temperature drop (when the bias control loop 52 is in operation), or a sudden increase in the magnitude of the bias current (when the temperature control loop 40 is in operation), either of which may be improperly interpreted as a refrigerant gas detection. Continued operation of the sensing device at the unnecessarily high peak temperature also contributes to the foreshortening of the sensing device lifespan. It is thus critical to lower the temperature of the sensing device 11 to the desired operating temperature as soon as re-polarization is complete and reliable operation may be ensured. This temperature adjustment may be based on the status of the bias current, which decreases sharply in a significantly depolarized sensing device 11 under constant temperature conditions but settles out asymptotically to a constant magnitude as re-polarization is completed. It has been determined that reliable operation of the detector 5 may be ensured once the bias current drops sufficiently close to its asymptotic value. Because this asymptotic value may vary, this state may be accurately derived automatically by measuring the negative slope of the bias signal while the temperature is held in excess of the desired operating temperature. Once the slope has decreased to a predetermined value, which may be determined empirically, warm-up of the sensing device 11 is complete and normal operation of the detector 5 may be initiated.

It has been found that the combined steps of the methodology described hereinabove reduces the amount of time required for the safe warm-up of the refrigerant sensor 5 from a minute or more to a range of less than two seconds for a sensor that has been recently used to approximately 15 seconds for a sensor that has been idle for many weeks. It should be obvious that although this ramped technique for warming up the refrigerant detector 5 may be most effectively implemented using a microprocessor, an approximation may also be implemented manually. If a microprocessor is utilized, it may, of course, be used to implement the other functions of the respective temperature and bias current control loops 40, 52 as well. It should also be obvious that similar warm-up procedures may also be utilized for a detector 5 using only a temperature control loop 40.

Once the refrigerant detector 5 has been warmed up, the user may choose to set, either directly or via microcode, the controllable switch 62 to route the output of the bias current control loop 52 to the temperature error subtractor 48. A desired bias current may then be input into the refrigerant detector 5 using the bias current input means 56. Alternatively, the controllable switch 62 may be adjusted automatically from one position to the other on the occurrence of some predetermined phenomenon, such as the negative slope of bias signal dropping to a predetermined value. Once the switch is adjusted to route the output of the bias current control loop 52 therethrough, the bias current control loop 52 converts and amplifies the voltage potential across the resistor 36 and subtracts that signal from the desired set point signal provided from the bias current input means 56. The resulting error signal is amplified and phase-compensated by the second processing means 60 and then provided as the reference temperature setting to the temperature control loop 40 via the controllable switch 62. Significantly, a separate set of empirically-determined filter coefficients is required for the second processing means 60 from the ones required for the first processing means 50.

If the preferred method of warming up the sensing device 11 is utilized, then the initial entered bias current magnitude is the magnitude of the bias current when the bias control loop 52 is first switched in. Typically, the bias current magnitude at that time is considerably greater than the desired bias current magnitude described previously. However, the bias current may then be ramped down quickly until the desired bias current magnitude is reached, and the bias current is then held steady at that level as described previously.

Significantly, the transition of the detector 5 from the temperature control mode used to warm up the sensing device 11 to the bias current control mode used for normal operation usually results in a significant drop in the temperature of the sensing device 11 as the sensing device 11 drops from the predetermined peak temperature used for re-polarization to an operating temperature which is predominantly dependent upon the magnitude of the bias current and the age of the sensing device 11. Over the life of the sensing device 11, this "desired operating temperature," which in this embodiment is actually whatever temperature is required to maintain the desired bias current magnitude, gradually creeps upward until it nearly equals the maximum safe operating temperature of the sensing device 11, at which point the sensing device 11 must be replaced.

Figure 5:
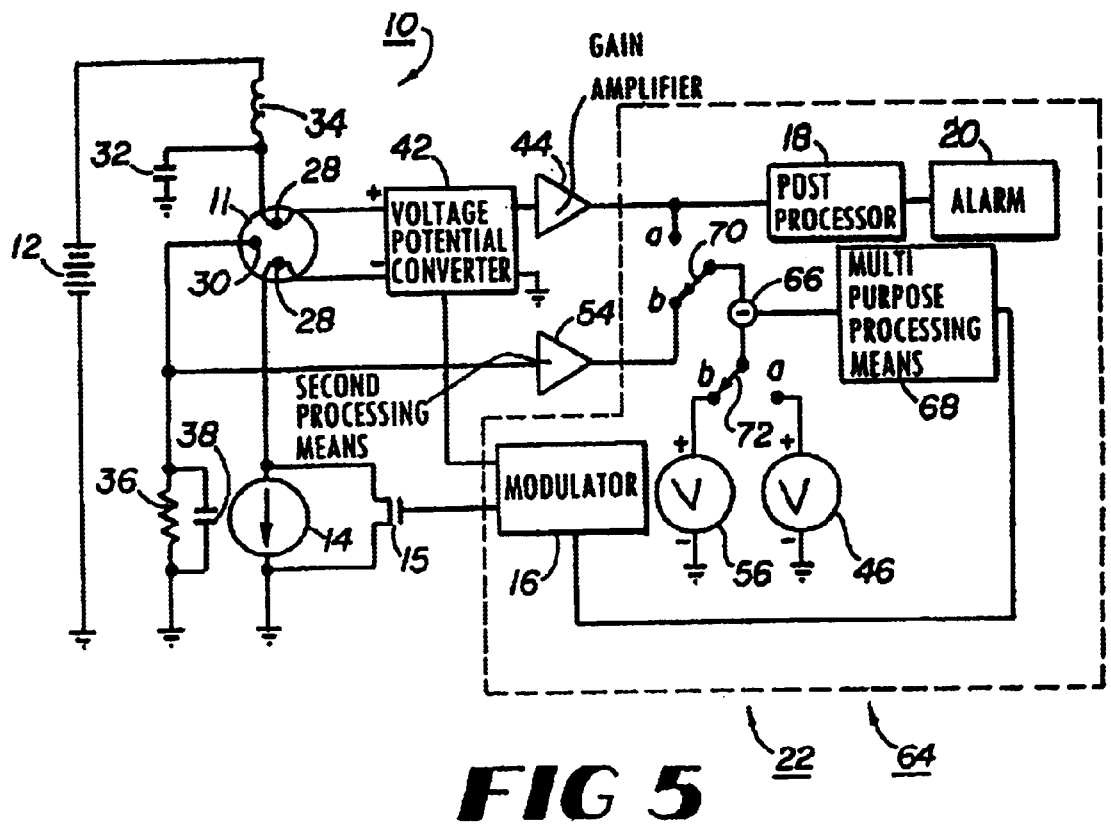
FIG. 5 is a schematic diagram of a variation of the third preferred embodiment of the heated electrode refrigerant detector of FIG. 4.

In a variation of the third embodiment of the present invention, shown in FIG. 5, the temperature control loop 40 and the bias current control loop 52 are combined into a single loop 64. The single control loop 64, which once again may be implemented by either digital (microprocessor and code) or analog (discrete components) means, includes a voltage potential converter 42, first and second gain amplifiers 44, 54, temperature and bias current input means 46, 56, a multi-purpose subtractor 66, a multi-purpose processing means 68 and a pair of controllable switches 70, 72. Similarly to the variation of the third embodiment shown in FIG. 4, the voltage potential converter 42 is connected to the anode contacts 28 and the modulator 16 and converts the differential temperature signal present at the anode contacts 28 into a single-ended signal in synchronization with the "off" time of the modulator 16. The output of the voltage potential converter 42 is connected to the first gain amplifier 44, the output of which is connected to one input of the first controllable switch 70. The other input of the first controllable switch 70 is connected to the output of the second gain amplifier 54, the input of which is connected to the cathode contact 30 of the sensing device 11.

The output of the first controllable switch 70 is connected to the input of the multi-purpose subtractor 66, the other input of which is connected to the output of the second controllable switch 72. The respective inputs of the second controllable switch 72 are connected to the temperature and bias current input means. The output of the subtractor 66 is connected to the input of the multi-purpose processing means 68, the output of which is connected to the modulator 16. Like the modulator 16 of the variation of the third embodiment shown in FIG. 4, the output of the modulator 16 is connected to the switch 15 in order to modulate the current generated through the anode coil 26.

In operation, the user turns the refrigerant detector 5 on and sets the controllable switches 70, 72 to route the output of the first gain amplifier 44 and the signal from the temperature input means 46 to the multi-purpose subtractor 66. Preferably, both controllable switches 70, 72 may be adjusted simultaneously using any suitable control apparatus or method, such as a single mechanical control or transistor which is operatively connected to both controllable switches 70, 72, on a command from a microprocessor, or the like. The user may then input a desired temperature into the refrigerant detector 5 using the temperature input means 46, and proceed to warm up the sensing device 11 quickly using the method described with regard to the first variation of the third preferred embodiment.

Once the refrigerant detector 5 has been warmed up, the user may choose to simultaneously adjust the controllable switches 70, 72 to route the output of the second gain amplifier 54 and the signal from the bias current input means 56 to the multi-purpose subtractor 48. As described previously, the switches 70, 72 may be adjusted automatically as soon as the desired operating temperature is reached, and the user may then input a desired bias current into the refrigerant sensor 5 using the bias current input means 56, or the desired bias current may be input automatically by the microprocessor. Once the switches 70, 72 are so adjusted, the voltage potential across the resistor 36 is amplified and subtracted from the desired set point signal provided from the bias current input means 56, and the resulting error signal is amplified and phase-compensated by the multi-purpose processing means 60 and provided to the modulator 16. Thereafter, the refrigerant detector 5 may be used as described with regard to the second preferred embodiment to indicate the presence of halogen molecules in an area of interest. It should be noted that the multi-purpose processing means 60 may utilize two separate sets of empirically determined coefficients as described previously, the set in use being selected by the position of the switches 70, 72, or may instead utilize only a single set of empirically determined coefficients which are valid for either loop, thus simplifying the control by making the state of the switch irrelevant.

In a further feature of the present invention, the refrigerant detector 5 may also utilize an improved sensing device 111 having a pair of bus bars and a pair of additional contacts to create a low-noise, low-impedance device with a configuration commonly known as a "Kelvin Connection." FIG. 6 is a detailed diagrammatic view of an improved sensing device 111 suitable for use in the primary detection circuits 10 of FIGS. 2–4. The improved refrigerant sensor 111 includes a anode/cathode assembly of similar construction to the prior art sensing device 11, a pair of bus bars 125, a pair of supply or drive contacts 128 and a pair of temperature sense or Kelvin contacts 129. The ends of the anode coil 26 may be attached to the centers of respective bus bars 125. One supply contact 128 is connected to an end of each bus bar 125, and one temperature sense contact 129 is connected to the opposite end of each bus bar 125. As with the prior art sensing device 11, the exposed end of the cathode wire 24 is connected to the cathode contact 30 to create a total of five contacts. Each contact is mounted through the base 131 of a TO-5 transistor can, which further includes a sample air exhaust hole 133 disposed adjacent the anode/cathode assembly.

It should be obvious to one of ordinary skill that although as described and illustrated the bus bars 125 are separate elements from the drive contacts 128 and the temperature sense contacts 129, any of a variety of alternative constructions may instead be used. For example, each bus bar 125 and its corresponding contacts 128, 129 may be formed of a single piece of "U"-shaped metal, referred to herein as a U-pin. Each end of the anode coil 26 may be attached to the midsection of a respective U-pin, and the downwardly extending ends of the "U" would form the contacts 128, 129 extending from the base 131 of the TO-5 can. In another variation, an off-the-shelf TO-5 assembly having five vertical, but separate, pins may be utilized by bending the upper ends of two pairs of the pins toward each other so that they touch underneath the can. Each end of the anode coil 26 may then be attached to a respective pair of pins at the junction formed by the ends of the pins. Additional variations for the bus bar arrangement will also be readily apparent to one of ordinary skill in the art.

The supply contacts 128 are utilized to supply the heating current from the battery power supply 12 to the anode coil 26. The temperature sense contacts 129 are utilized to measure the voltage potential across the anode coil 26 during the "off" periods of the switch 15 during the "off" periods of the switch 15. As described previously, the voltage potential across the anode coil 26 is proportional to the resistance of the anode coil 26, which is approximately linearly related to the temperature of the sensing device 111 and thus provides a direct indicator of the absolute temperature of the sensing device 111. The use of these additional contacts helps to optimize the temperature sensing of the anode coil 26 while eliminating non-linearities due to lead resistance and noise due to dirty or high-impedance contacts. It should be clear to one of ordinary skill in the art that this improved sensing device 111 may be used by any heated electrode refrigerant sensor implementation in which accurate information about the temperature of the sensing device 111 is desired. However, if the improved sensing device 111 is not readily available or if other factors make its use undesirable, it should likewise be clear that the various control loops described herein may instead make use of an ordinary three-terminal sensing device as previously described.

It will therefore be readily understood by those persons skilled in the art that the present invention is susceptible of broad utility and application. Many embodiments and adaptations of the present invention other than those herein described, as well as many variations, modifications and equivalent arrangements, will be apparent from or reasonably suggested by the present invention and the foregoing description thereof, without departing from the substance or scope of the present invention. Accordingly, while the present invention has been described herein in detail in relation to its preferred embodiments, it is to be understood that this disclosure is only illustrative and exemplary of the present invention and is made merely for purposes of providing a full and enabling disclosure of the invention. The foregoing disclosure is not intended or to be construed to limit the present invention or otherwise to exclude any such other embodiments, adaptations, variations, modifications and equivalent arrangements, the present invention being limited only by the claims appended hereto and the equivalents thereof

What is claimed is:

1. A gas detector, operative in conjunction with a power source, for sensing the presence of at least one predetermined gas, the gas detector comprising:
    a detection circuit, the detection circuit including a sensing device having first and second electrodes, wherein the first electrode is connected to the power source for heating the first electrode;
    a temperature controller operatively connectable to the detection circuit for maintaining a temperature of the first electrode at a predetermined magnitude;
    a current controller operatively connectable to the detection circuit for maintaining a electrical current in the second electrode at a predetermined magnitude; and
    a switch adjustable between at least two positions, wherein in a first switch position the temperature controller is operatively connected to the detection circuit and in a second switch position the current controller is operatively connected to the detection circuit, the position of the switch is determined on the basis of an operating condition of the gas detector.

2. The gas detector as in claim 1, wherein the switch is located internally to the gas detector.

3. The gas detector as in claim 1, wherein the switch is located externally on the gas detector.

4. A method of controlling a gas detector for sensing the presence of at least one predetermined gas, the gas detector having a heated first electrode and a second electrode, herein the method comprises the steps of:
    heating the first electrode to a predetermined absolute temperature;
    upon reaching the predetermined absolute temperature, placing the electrodes in a test location;
    upon being exposed to one of the predetermined gases, generating an increased electrical current in the second electrode; and maintaining the first electrode at substantially the predetermined absolute temperature while placing the electrodes in the test location and while generating the increased current.

5. The method of claim 4, further including the steps of selecting the predetermined absolute temperature and providing an indication of the predetermined absolute temperature to the gas detector.

6. The method of claim 5, wherein the step of providing an indication of the predetermined absolute temperature takes place while the detector is being operated.

7. The method of claim 5, wherein the step of providing an indication of the predetermined absolute temperature includes the step of predefining the predetermined absolute temperature during manufacturing.

8. The method of claim 5, wherein the step of providing an indication of the predetermined absolute temperature includes the step of entering the predetermined absolute temperature into the gas detector.

9. The method of claim 4, wherein the amount of heat applied to the first electrode is dependent on a duty cycle, and wherein the step of maintaining the first electrode at substantially the predetermined absolute temperature includes the step of adjusting the duty cycle.

10. The method of claim 4, further including the step of monitoring the actual temperature of the first electrode, and wherein the step of maintaining the first electrode at substantially the predetermined absolute temperature includes the steps of reducing the temperature of the first electrode upon determining that the actual temperature exceeds the predetermined absolute temperature and raising the temperature of the first electrode upon determining that the actual temperature is below the predetermined absolute temperature.

11. A gas detector, operative in conjunction with a power source, for sensing the presence of at least one predetermined gas, the gas detector comprising:

an anode/cathode assembly coated with a ceramic material, the anode/cathode assembly including a cathode wire and an anode wire at least partly surrounding the cathode wire, wherein the anode wire has opposing ends and wherein one of the anode wire ends is electrically connected to the power source;

a pair of supply contacts electrically connected to the respective ends of the anode wire;

a pair of temperature sense contacts electrically connected to respective ends of the anode wire;

a cathode contact electrically connected to an end of the cathode wire;

a temperature-sensing circuit electrically connected to at least one of the temperature sense contacts for monitoring the temperature of the anode/cathode assembly; and a bias current-sensing circuit electrically connected to the cathode contact.

12. A system for controlling a gas detector for sensing the presence of at least one predetermined gas, the gas detector having a heated first electrode and a second heated electrode, comprising:

means for heating the first electrode to a predetermined absolute temperature;

means for placing the electrodes in a test location;

means for generating an increased electrical current in the second electrode; and means for maintaining the first electrode at substantially the predetermined absolute temperature while placing the electrodes in the test location and while generating the increased current.

13. The system as in claim 12, further comprising means for selecting the predetermined absolute temperature and means for indicating the predetermined absolute temperature of the gas detector.

14. The system as in claim 13, wherein the means for providing the indication of the predetermined absolute temperature while the detector is being operated.

15. The system as in claim 13, wherein the means for providing the indication of the predetermined absolute temperature includes a predefined absolute temperature.

16. The system as in claim 15, wherein the predefined absolute temperature is determined at the time of manufacturer.

17. The system as in claim 13, further comprising means for entering the predetermined absolute temperature into the gas detector.

18. The system as in claim 12, wherein the amount of heat applied to the first electrode is dependent on a duty cycle and wherein the means for maintaining the first electrode at substantially the predetermined absolute temperature comprises means for adjusting a duty cycle.

19. The system of claim 12, further comprising means for monitoring the temperature of the actual temperature of the first electrode, means for reducing the temperature of the first electrode upon determining that the actual temperature exceeds the predetermined absolute temperature and means for raising the temperature of the first electrode upon determining that the actual temperature is below the predetermined absolute temperature.

20. The gas detector as in claim 19, wherein the internal switch is implemented with discrete components.

* * * * *

UNITED STATES PATENT AND TRADEMARK OFFICE
CERTIFICATE OF CORRECTION

PATENT NO. : 6,644,098 B2
DATED : November 11, 2003
INVENTOR(S) : Dennis Cardinale et al.

It is certified that error appears in the above-identified patent and that said Letters Patent is hereby corrected as shown below:

Title page,
Item [56], References Cited, FOREIGN PATENT DOCUMENTS, insert
-- WO   9924887 A     05-20-99      WIPO --.

Signed and Sealed this

Twenty-seventh Day of September, 2005

JON W. DUDAS
*Director of the United States Patent and Trademark Office*